United States Patent [19]

Raghavachari

[11] 4,192,919
[45] Mar. 11, 1980

[54] BLOOD SAMPLING AND CULTURING KIT

[75] Inventor: Srinivas T. Raghavachari, Chicago, Ill.

[73] Assignee: MPL, Inc., Chicago, Ill.

[21] Appl. No.: 816,371

[22] Filed: Jul. 18, 1977

Related U.S. Application Data

[63] Continuation-in-part of Ser. No. 797,841, May 17, 1977, abandoned.

[51] Int. Cl.² .............................................. A61M 5/315
[52] U.S. Cl. .................................... 435/292; 435/810; 128/764; 128/218 D; 128/218 PA; 137/199; 422/101; 435/294
[58] Field of Search ............... 195/127, 142, 126, 139; 128/2 F, DIG. 5, 218 D, 218 PA; 137/199; 422/101

[56] References Cited

U.S. PATENT DOCUMENTS

| | | | |
|---|---|---|---|
| 2,607,344 | 8/1952 | Brown | 128/218 D |
| 3,682,596 | 8/1972 | Stone | 422/101 |
| 3,831,601 | 8/1974 | Kessell | 128/218 PA |

*Primary Examiner*—Lionel M. Shapiro
*Attorney, Agent, or Firm*—Kinzer, Plyer, Dorn & McEachran

[57] ABSTRACT

A blood sampling and culturing kit for use with blood culture bottles containing a culture media under vacuum and evacuated specimen tubes. The kit includes a sterile blood collector tube assembly for transferring a blood sample from a patient into the blood culture bottles and evacuated specimen tubes; the tube assembly comprises a venipuncture needle having first and second cannulas projecting in opposite directions from a first hub and a bottle connection needle including first and second cannulas projecting in opposite directions from a second hub, with a valve in the second hub that is opened and closed by movement of one cannula. A flexible plastic tube receives the second cannula of each needle, completing a sealed passage between the needles. The kit also includes two vent control devices; each device includes a tubular housing having a central bore open at its opposite ends. A cannula projects outwardly from one end of the housing to connect the vent control device to a bottle by piercing the bottle stopper. There is a vent control element at the opposite end of the housing. In one vent control device, the vent control element is an air-permeable sterile filter consisting of a sheet of spunbond olefin; in the other, the vent control element is a plug seal slidably mounted in the central bore of the housing, which opens the housing in response to a buildup of excessive pressure within the bottle.

7 Claims, 9 Drawing Figures

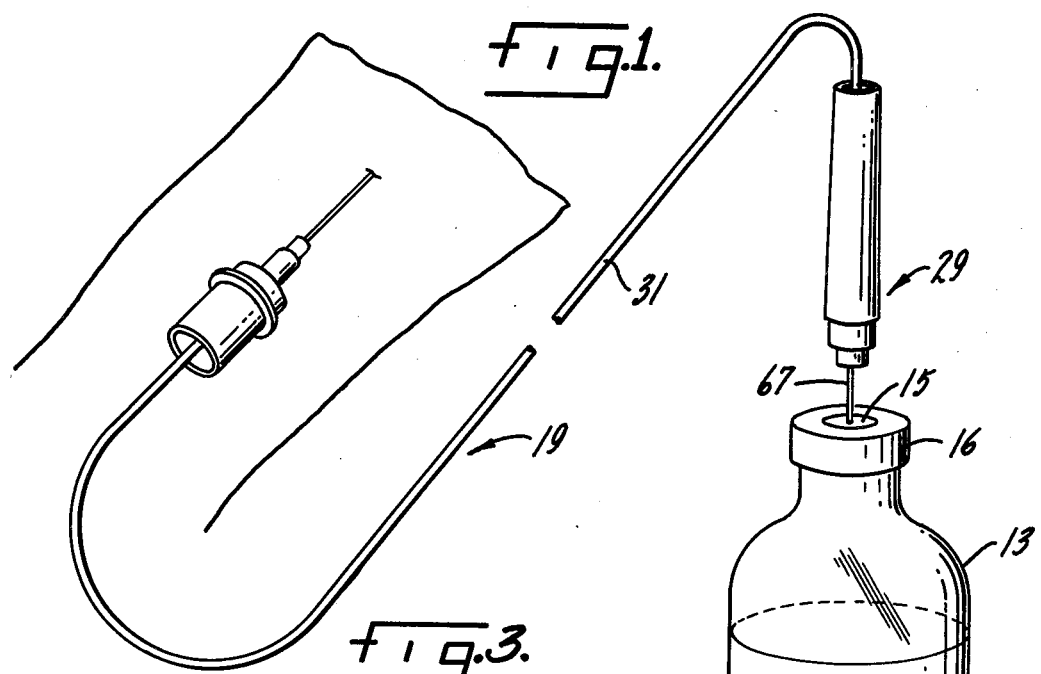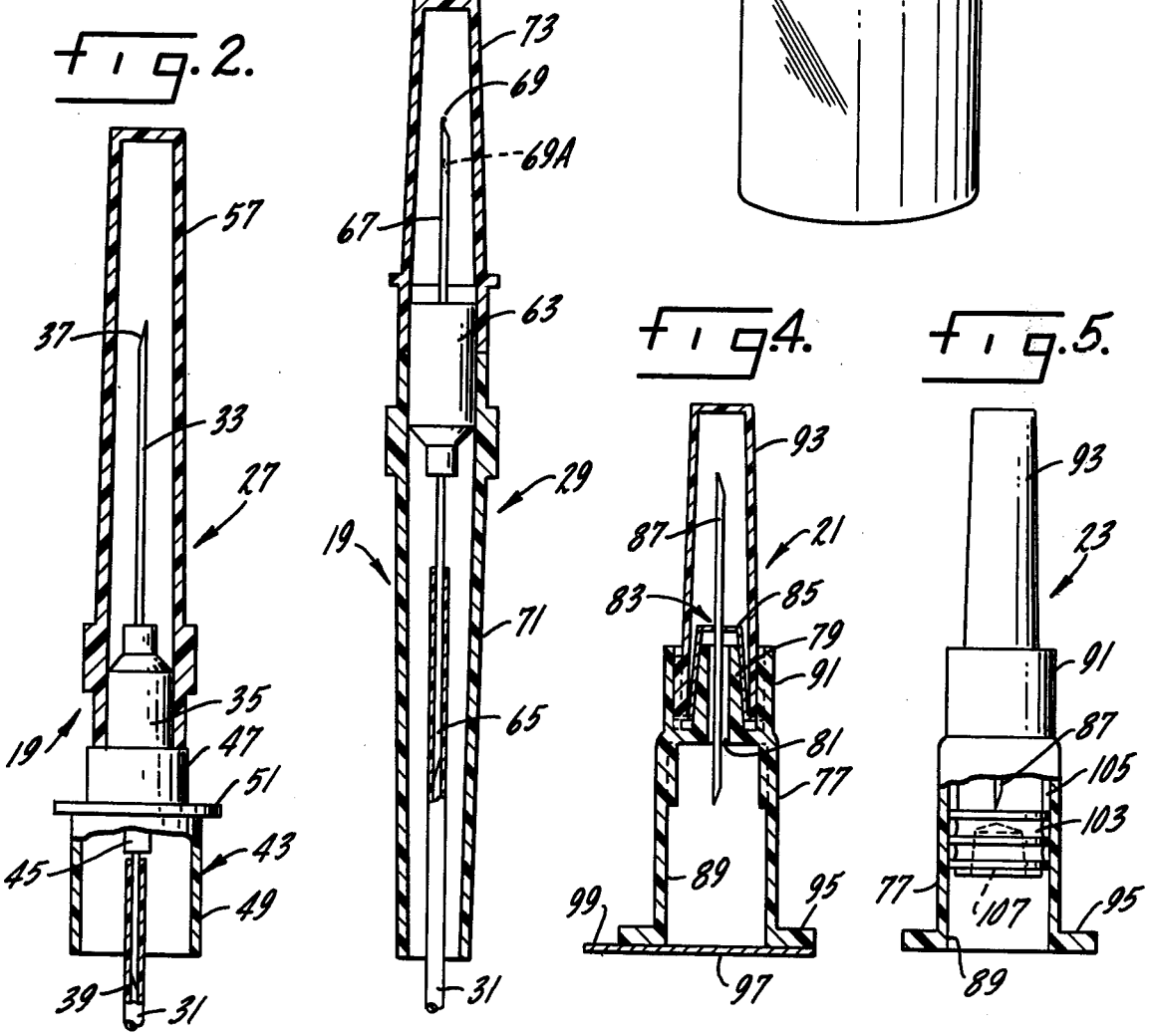

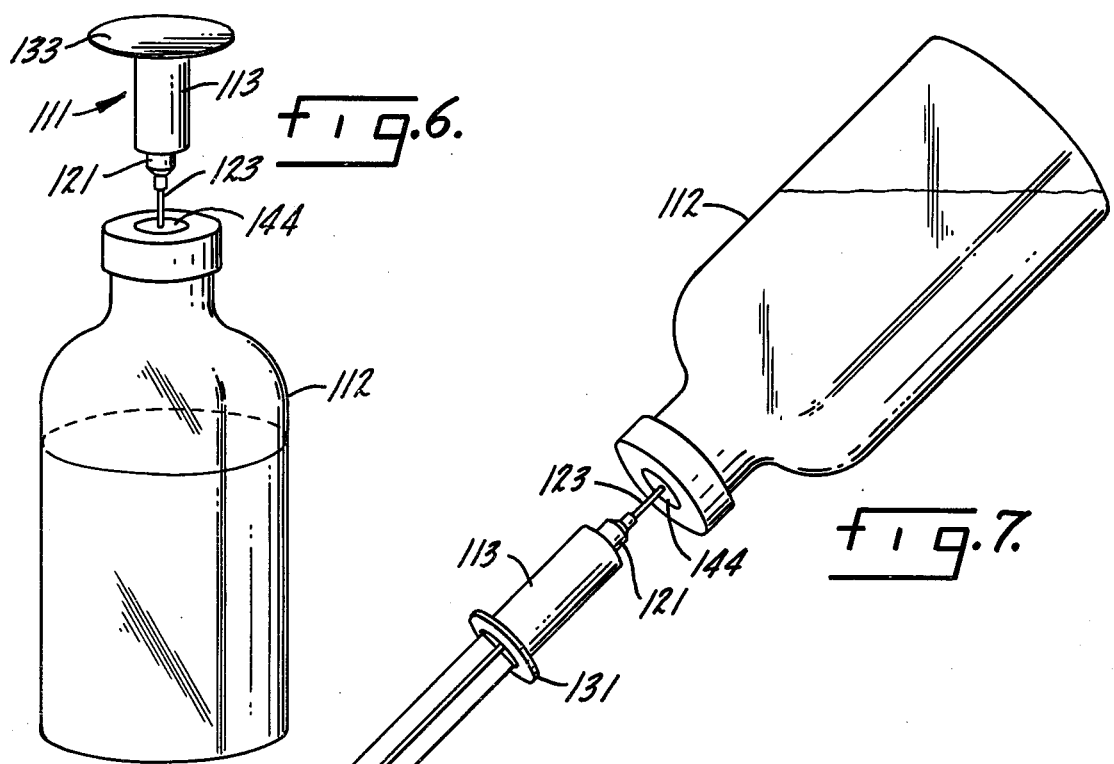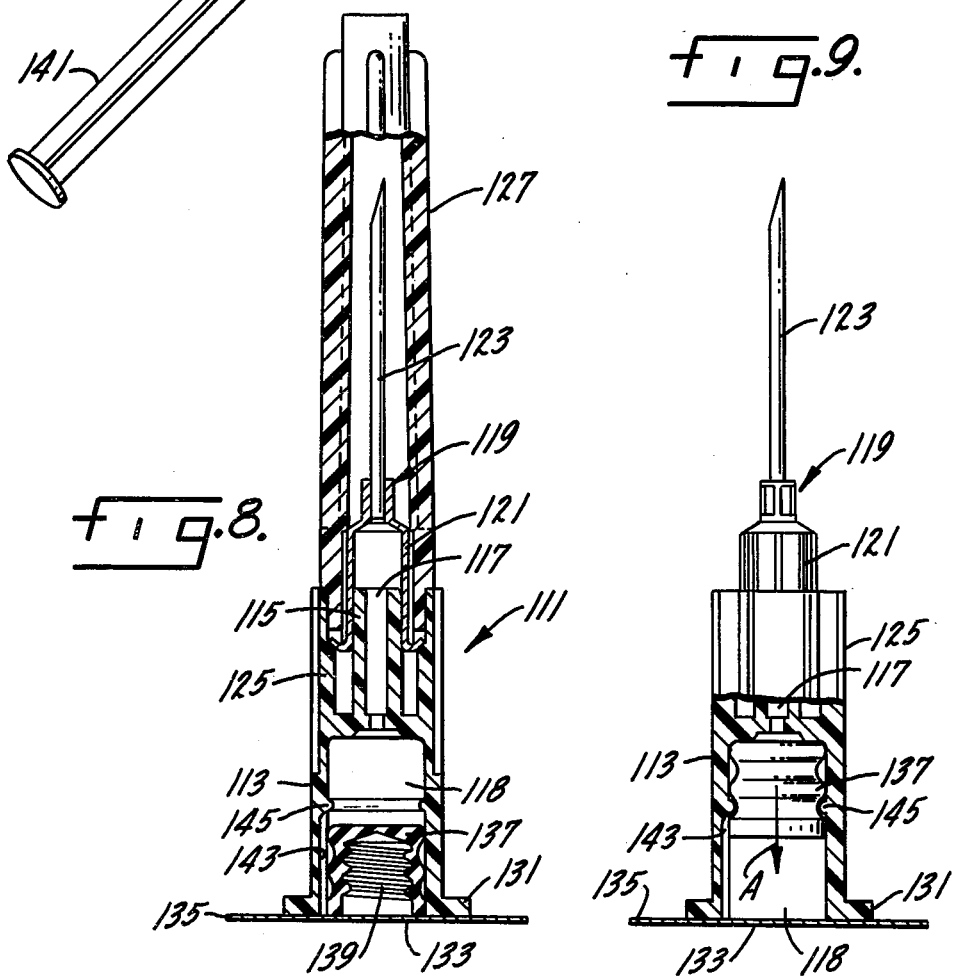

BLOOD SAMPLING AND CULTURING KIT

This is a continuation-in-part of my co-pending application Ser. No. 797,841, filed May 17, 1977, now abandoned.

BACKGROUND OF THE INVENTION

Blood culturing by the broth culture technique is an important diagnostic tool in modern medicine. It is used to determine difficult to identify infections, especially those which have not responded to treatment by the normally used antibiotics. In the broth culture technique, blood is withdrawn aseptically from a pateint's vein and is added to a blood culture bottle containing a culture medium designed to provide the nutritional and environmental requirements of the bacteria commonly encountered in bacteremia.

Blood is added to a blood culture bottle using either a closed system or an open system. In the closed system, a sterile blood collecting tube is used, permitting blood to enter the bottle directly from the patient. In the open system, blood is collected with a sterile needle and syringe and is either injected into the blood culture bottle at the bedside or the blood specimen is mixed with an anticoagulant for transporting to the laboratory where it is injected into the blood culture bottle.

A conventional sterile blood collecting tube includes a relatively thick walled plastic tube having a needle located at each end thereof. One needle, which is inserted into a patient's vein, is a venipuncture needle, while the other needle is inserted through the pierceable stopper of a blood culture bottle. The needles of a sterile blood collecting tube have cannulas which are anchored in machined metal hubs. The hubs extend into and are anchored in the ends of the plastic tube. Removable plastic sheaths are provided for each needle with the venipuncture needle having a sheath closed at one end, while the sheath for the blood culture bottle needle is open at both ends and contains a wad of sterile cotton.

In using the conventional sterile blood collecting tube, it is necessary for the medical person to squeeze the thick walled plastic tube, either by hand or with a hemostat, to prevent the discharge of blood from the tube during the insertion and removal of the stopper piercing needle from the blood culture bottle. Frequently, during the taking of multiple samples, blood is accidentally discharged from the stopper piercing needle, thus creating hygenic problems in the patient's environment.

The injected culture bottle is vented for aerobic culturing, or is left unvented for anaerobic culturing. The bottle is usually incubated at 35° C. for a period varying from 7 to 21 days. During the incubation time, the bottle is visually inspected, gram-stained and subcultured, using suitable media and incubation conditions in order to determine if the growth of a microorganism has occurred.

The number and frequency of specimen collections is usually based upon the particular clinical situation. Usually, two blood culture bottles, each of which preferably contains 100 ml of a culture medium, should each be innoculated with 5 to 10 ml of blood. One bottle should be vented for aerobic incubation and one bottle should be left unvented for anaerobic incubation. The blood culture bottles customarily contain a soy broth medium and carbon dioxide under negative pressure.

After the blood is injected into the blood culture bottles, it is necessary to vent the bottle used for aerobic incubation. Venting has customarily been accomplished through the use of a sterile disposable 20-22 gauge needle having sterile absorbent cotton packed in the needle hub. The needle is inserted through the rubber stopper in the outlet of the blood culture bottle. This vent permits the introduction of air into the bottle, with the sterile cotton functioning to prevent the entry of airborne bacteria. However, this method has not proved entirely satisfactory since the sterile cotton is not completely effective in preventing the entry of airborne bacteria into the blood culture bottle.

Subculturing has required the use of a sterile needle and syringe with the needle attached to the syringe being inserted through the rubber top of the blood culture bottle to withdraw the required amount of innoculated culture medium.

The blood culture bottle used for anaerobic incubation is not vented under present practice. The bacterial action in the sealed bottle generates gases, resulting in a pressure buildup in the bottle. The pressure may go as high as 80 psi. In addition to the danger of rupture of the bottle, the pressure buildup in an anaerobic bottle prevents subculturing until the pressure is relieved.

The danger of backflow of blood into a patient's vein from an evacuated specimen tube during the taking of multiple blood samples exists under present practice. Because most specimen tubes in use are non-sterile, the reverse flow of blood into the patient presents a serious health hazard.

SUMMARY OF THE INVENTION

It is an object of the present invention, therefore, to provide a blood sampling and blood culturing kit, for use with blood culture bottles and evacuated specimen tubes, having a sterile blood collector tube assembly suitable for obtaining multiple blood samples, and which provides an automatic cutoff between samples to prevent accidental discharge of blood which could contaminate the patient's environment.

Another object of this invention is to provide a sterile blood collector tube assembly which minimizes the possibility of backflow of blood into a patient from an evacuated specimen tube during the taking of multiple blood samples.

A further object of the invention is a vent control device for use with an aerobic blood culture bottle and which prevents atmospheric contamination of the blood culture medium in the bottle.

Another object of the invention is to provide a new and improved vent control device for an aerobic blood culture bottle which facilitates subculturing of the blood culture medium.

Yet another object of the invention is to provide a new and improved vent control device for an aerobic blood culture bottle, utilizing a thin sheet of an air-permeable filter material which is more effective than the sterile cotton presently used as a filter material in needle hubs.

Another object of the invention is an improved vent control device, for use in anaerobic blood culturing, in which the vent control element relieves a buildup of excessive pressure within the blood culture bottle.

Another object of this invention is an improved vent control device that can be used for either aerobic or anaerobic venting simply by repositioning a plunger located in the device.

Another object of this invention is an improved vent control device which can also be used as a syringe for a subculturing procedure in which a specimen is removed from the blood culture bottle and accurately deposited in a designated portion of a culture plate.

Accordingly, the invention relates to a blood sampling and blood culturing kit for use with blood culture bottles of the type containing a culture medium, under vacuum, and having a pierceable stopper sealing each bottle and evacuated specimen tubes. The kit includes a sterile blood collector tube assembly for transferring one or more blood samples from a patient into blood culture bottles or evacuated specimen tubes. The sterile blood collector tube assembly includes a venipuncture needle at one end of the tube and having first and second cannulas projecting in opposite directions from a connector hub. Additionally, there is a stopper piercing needle at the other end of the tube which includes first and second cannulas projecting in opposite direction from a connector hub. A valve is positioned in the stopper piercing needle connector hub and the valve is opened and closed by sliding movement of the cannula which pierces the stopper. A thin flexible plastic tube slides over and tightly engages the second cannulas of the two needles at opposite ends thereof to complete a sealed passage between the two needles. The kit also includes vent control devices, one of which is adapted for aerobic blood culturing and the other which is adapted for anaerobic blood culturing.

Another modified form of vent control device can also be used as a syringe for a subculturing procedure in which a specimen is removed from the blood culture bottle and deposited on a culture plate. This modified form of vent control device is adaptable to both aerobic and anaerobic venting simply by relocating a plunger in the vent control device.

BRIEF DESCRIPTION OF THE DRAWINGS

FIG. 1 is a partial, somewhat schematic view of a sterile blood collector tube assembly of this invention, showing blood being transferred from a patient into a blood culture bottle;

FIG. 2 is a partial enlarged view of the venipuncture needle assembly shown in FIG. 1;

FIG. 3 is an enlarged view, partially in cross-section, of the culture bottle stopper piercing needle assembly shown in FIG. 1;

FIG. 4 is an enlarged cross-sectional view of a vent control device for an aerobic blood culture bottle;

FIG. 5 is an enlarged side elevational view, partially broken away, of a vent control device for an anaerobic blood culture bottle.

FIG. 6 is a perspective view of a modified vent control device of this invention inserted in venting position through the stopper of a blood culture bottle;

FIG. 7 is a perspective view of the vent control device of FIG. 6 in use as a syringe for withdrawing a sample of the contents of the blood culture bottle for further use in subculturing;

FIG. 8 is an enlarged cross-sectional view of the modified vent control device of FIG. 6 with its plunger positioned for aerobic venting; and FIG. 9 is an enlarged elevation view of the modified vent control device of FIG. 6, partially broken away and showing its plunger positioned for anaerobic venting.

DESCRIPTION OF THE PREFERRED EMBODIMENT

The blood culturing and sampling kit of this invention is intended for use with blood culture bottles 13 of the type containing a culture medium. Additionally, the kit can be used with evacuated blood specimen tubes, which are not shown but are commercially available. The blood culture bottles contain culture media designed to provide the nutritional and environmental requirements of the bacteria commonly encountered in bacteremia. The blood culture medium may be a tryptic soy broth. A carbon dioxide atmosphere under negative pressure is usually provided for the culture medium. The evacuated specimen tubes are usually non-sterile and are closed by pierceable rubber stoppers. The blood culture bottle is closed by a pierceable stopper 15 which is usually formed of a synthetic rubber. A metal or plastic annular shaped cover 16 is frequently provided to hold the stopper to the blood culture bottle.

The blood sampling and culturing kit of this invention includes a sterile blood collector tube assembly 19, shown in FIGS. 1, 2 and 3, vent control device 21 for an aerobic blood culture bottle, shown in FIG. 4, and vent control device 23 for an anaerobic blood culture bottle, shown in FIG. 5.

The sterile blood collector tube assembly 19 includes a venipuncture needle 27, a blood culture bottle penetrating needle 29, and a transparent plastic tube 31 of small diameter connecting the two needles. The tube assembly may be packaged in a sterile pouch for shipment to the user. The venipuncture needle 27 is shown in detail in FIG. 2 and includes a cannula 33 fastened as by crimping to a metal connector hub 35. The cannula extends beyond both axial ends of the hub but its projection in one direction is greater than its projection in the other direction. The ends 37 and 39 of the cannula are bevelled to provide sharpened points. A venipuncture needle of this construction is a commercially available item and can be used in sterile blood collector tube assembly of this invention without modification. Thus, a cost advantage is provided over the conventional sterile blood collecting tube which has needles using machined hubs. Cannula end 39 can be blunt if preferred.

The venipuncture needle 27 is mounted on a short plastic tubular grip 43 affording three coaxial plastic sleeves 45, 47 and 49. The grip 43 may be a molded plastic member ordinarily used as the nose end of a syringe. Sleeves 47 and 49 are joined by a radially extending disc 51, while plastic sleeve 45 extends through the disc and axially beyond the end of the sleeve 47. The shorter end 39 of the cannula 33 extends through the plastic sleeve 45; the hub 35 of the needle fits over the sleeve 45 and into the sleeve 47. The sleeve 45 is formed with a Luer taper to receive the needle hub.

A helical groove (not shown) may be formed in the inside wall of the sleeve 47 to receive tabs (not shown) formed on the metal hub 35. This permits threaded engagement of the needle hub with the plastic grip 43. The tube 31 fits tightly over the shorter end 39 of the cannula 33 and extends inside the sleeve 49. The disc 51 extends radially beyond the plastic sleeve 49 to provide a flange to improve gripping of the venipuncture needle assembly 27. The needle 27 may be fastened to the grip 43 in other conventional manners, but the foregoing is the preferred construction. A removable plastic sheath 57 encloses the longer end 37 of the needle 27 to maintain sterility. As is customary, the sheath may be taped to the grip 43.

The bottle stopper penetrating needle 29 (FIG. 3) utilizes a valved double cannula needle of the type described in U.S. Pat. No. 3,659,587, issued May 2, 1972. Needles of this type are available commercially and may be used in this invention without modification for cost savings. The valved double cannula needle includes a hub 63 formed of metal and having a longer cannula 65 secured to the smaller end of the hub. A shorter cannula 67 extends from the opposite end of the hub and is slidable relative to the hub to open and close a valve located inside the hub. When the shorter cannula 67 is in its extended position, the valve inside the hub 63 is closed and no liquid can pass through the needle 29. When the cannula 67 is slid to its retracted position, the valve inside the hub 63 is opened, permitting the flow of liquid through the needle assembly.

A barb 69 is formed at the bevelled end of the shorter cannula 67. The barb forces the cannula 67 to slide into the hub 63 to position 69A to open the valve when the cannula is pushed through a blood culture bottle stopper, and also functions to pull the cannula back to its outwardly extending position to close the valve whenever the cannula is removed from the bottle stopper. An open ended plastic sleeve 71 fits over and is fastened to the hub 63. The plastic tube 31 slides over and is fastened to the longer cannula 65, preferably by a friction engagement inside the sleeve 71. A removable plastic sheath 73 covers the shorter cannula 67 to maintain sterility. This sheath may be taped to the sleeve 71.

The sterile blood collector tube assembly 19 can also be used to take multiple blood samples which are collected in evacuated specimen tubes. The chances of backflow from the specimen tube into the patient's vein are less using the tube assembly 19 of this invention rather than with a conventional multiple sample needle and an evacuated specimen tube. Any reverse flow of blood due to equalization of pressures or disturbance of the patient's arm or for any other reason would have been seen in the plastic tubing long before any contaminated blood (contaminated by contact with the non-sterile specimen tube) would return to the patient's vein.

The blood collecting tube assembly 19 can be used for collecting blood into blood culture bottles and into evacuated specimen tubes. Thus, a collecting needle is inserted into the patient's vein only one time for both purposes. A totally closed and aseptic system is provided which transfers blood directly from the patient into the container. In practice, the evacuated specimen tubes are filled first, then the aerobic blood culture bottles and finally the anaerobic blood culture bottles. This insures that no air is introduced into the anaerobic blood culture bottle.

The vent control device 21, shown in FIG. 4, is intended to vent an aerobic blood culture bottle or vial. It includes a plastic tubular housing 77 having a needle hub mount 79 at one end thereof. The exterior of the mount 79 has a standard Luer taper to receive a needle hub in tight fitting relation. A passage 81 extends through the needle hub mount to receive a needle cannula. A conventional needle assembly 83 having a metal hub 85 with a cannula 87 affixed thereto fits over the needle hub mount 79 and is affixed thereto. One end of the cannula extends outwardly beyond the end of the tubular housing 77 while the other and shorter end of the cannula extends through the passage 81 and into the central bore 89 of the tubular housing 77. The metal hub 85 may be affixed to the hub mount 79 by any conventional means such as an adhesive, a press fit, etc. An outer sleeve 91 surrounds the needle hub mount 79, and this sleeve may be equipped with a helical thread, not shown, to receive tabs affixed to the hub 85 in a threaded engagement. A removable protective sheath 93 of plastic seats in the annular space between the hub mount 79 and the sleeve 91 to maintain sterility of the cannula.

An annular flange 95 is formed at the opposite end of the tubular housing 77 at the inlet to the central bore 89. A filter element consisting of an air-permeable membrane 97 is attached to the annular flange 95 and covers the inlet to the central bore 89 of the tubular housing. A suitable membrane may be formed of a spunbonded olefin material which is sold by E. I. Dupont De Nemours and Company under the trademark "TYVEK". The membrane is coated on one side with a thermoplastic material so that it can be heat sealed to the annular flange 95. A tab portion 99 of the membrane extends outwardly beyond the flange to facilitate removal of the membrane from the flange.

In use, the sheath 93 is removed from the vent control device 21 and the exposed cannula 87 is inserted through the stopper 15 of a blood culture bottle 13 containing a blood sample and a culture medium. The vent control device permits the entry of air into the blood culture bottle as required for aerobic culturing. The membrane 97 prevents the entry of airborne bacteria into the bottle. Subculturing, which involves the transfer of the liquid from the bottle 13, can readily be accomplished by removal of the membrane 97 from the tubular housing 77. Removal of the membrane is facilitated by the tab 99 which can be grasped with the fingers. The liquid to be transferred for subculturing flows through the end of the cannula 87 which projects into the bore 89 of the housing 77. The extension of the cannula into the bore 89 of the housing will tend to direct the liquid away from the inside wall of the bore, thereby avoiding spillage of the liquid during transferring for subculturing.

The vent control device 23, shown in FIG. 5, is similar in construction to the vent control device 21 of FIG. 4. The only difference being that a membrane is not applied to the annular flange 95 of the device 23. Instead, a plunger 103 formed of rubber or other suitable material is slidably mounted inside the central bore 89 of the plastic housing 77. The plunger engages stops 105, integrally formed in the wall of the housing 77, to prevent the plunger from being impaled on the cannula 87.

Vent control device 23 is used to relieve pressure buildup in blood culture bottles during anaerobic culturing. The growth of bacteria during incubation creates carbon monoxide, carbon dioxide, methane, etc., causing pressures as high as 80 psi to develop in the blood culture bottles. Pressures of this magnitude frequently will blow the stopper out of the blood culture bottle, presenting a physical hazard to personnel and creating unsanitary conditions in the laboratory. When the cannula 87 of the air vent device 23 extends through the stopper 15 and into a blood culture bottle 13, any pressure buildup in the bottle will move the plunger 103 along the bore 89 of the tubular housing 77, thus relieving the pressure. When the pressure has developed to the point that the plunger is blown out of the bore 89, there will be a sufficient flow of gas out of the cannula 87 to maintain the anaerobic atmosphere in the blood culture bottle. As previously discussed, the projection of the cannula 87 into the bore 89 of the tubular housing 77 aids in subculturing of the culture medium.

The plunger 103 may be of the type used in syringes and which has a threaded bore 107 facing the inlet end of the central bore 89 of the tubular housing. A threaded plunger rod (not shown) also of the type used with syringes may be used to remove the plunger. It may be desirable to remove the plunger for subculturing at times when there is either no buildup of pressure in the blood culture bottle or inadequate buildup to blow the plunger out of the bore 89.

The combination vent control and syringe subculturing device 111, shown in FIGS. 6, 7, 8 and 9 of the drawings, is intended for use in venting and in subculturing an aerobic blood culture vial or bottle 112. It includes a tubular housing 113, preferably formed of molded plastic, having a needle hub mount 115 located at one end thereof. The exterior of the needle hub mount 115 has a standard Luer taper to receive a needle hub in fluid-tight fitting relation. A passage 117 extends through the needle hub mount to connect with the needle hub and with the central bore 118 of the housing 113. A conventional needle assembly 119 having a hub 121 with a cannula 123 affixed thereto fits over the needle hub mount 115 and is fastened thereto. The needle hub 121 may be fastened to the mount 115 in any conventional manner, such as by the use of an adhesive, a press fit, etc. The cannula 123 extends outwardly beyond the needle hub mount 115. An outer sleeve 125 encircles the needle hub mount 115 and defines an annular space therebetween. A removable protective sheath 127, preferably formed of molded plastic, seats in the annular space between the needle hub mount 115 and the outer sleeve 125 and may be sealed by tape (not shown) to the outer sleeve to maintain the sterility of the cannula.

An annular flange 131 is formed at the opposite end of the housing 113 at the inlet to the central bore 118. A filter element consisting of an air-permeable membrane 133 is attached to the flange 131 and covers the inlet to the central housing bore 118. A suitable membrane may be formed of a spunbonded olefin material of the type previously described. The membrane 133 is coated on one side with a thermoplastic material so that it can be heat sealed to the flange 131. The membrane extends outwardly beyond the flange, forming an annular portion 135 which can be grasped to facilitate removal of the membrane from the flange.

A plunger 137 formed of rubber or other suitable material is slidably mounted inside the central bore 118 of the tubular housing 113. There is a tight, sealing fit between the inner surface of the bore 118 and the outermost surfaces of the plunger 137. The plunger 137 preferably is of the type used in syringes, and has a threaded bore 139 facing the membrane 133. A threaded rod 141, also of the type conventionally used with syringes, threads into the bore 139 and is used to reciprocate the plunger in the bore.

In the arrangement shown in FIG. 8, the plunger 137 is positioned immediately adjacent the membrane 133. An axially extending slot 143 is cut in the inner wall of the central bore 118 and extends from the inlet of the central bore for a distance slightly greater than the length of the plunger 137. A rib 145 is formed on the inner wall of the central bore immediately inwardly of the slot 143. The slot 143 provides a bypass for the plunger, allowing the vent control device 111 to be used for aerobic venting of a blood culture bottle or vial. If the vent control device is to be used for anaerobic venting, the plunger 137 is positioned farther inwardly of the bore as shown in FIG. 9, where it blocks communication between the bypass slot 143 and the needle hub passage 117. Thus, the same vent control device 111 can be used for aerobic or anaerobic venting, depending upon the positioning of the plunger 137 in the central bore 118 of the tubular housing 113.

In use, the sheath 127 is removed from the vent control and subculturing device 111 and the exposed cannula 123 is inserted through a stopper 144 of a blood culture bottle containing a blood sample and a blood culture medium, as shown in FIG. 6. If the blood sample is undergoing aerobic culturing, a vent control device 111 of the type having its plunger 137 positioned adjacent the membrane 133 (FIG. 8) is used. This location of the plunger uncovers the bypass slot 143. The vent control device permits the passage of air into the blood culture bottle as required for aerobic culturing while the membrane 133 prevents the entry of airborn bacteria into the culture medium.

Subculturing, which requires the transfer of a small amount of the liquid from the blood culture bottle to a culture plate, can readily be accomplished by removal of the membrane 133 from the annular flange 131 of housing 113. Removal of the membrane is facilitated by the annular portion 135 of the membrane, which projects beyond the periphery of the flange 131. A rod 141 is threaded into the bore 139 of the plunger 137 so that the plunger can be reciprocated to draw liquid from the blood culture bottle into the central bore 118 of the tubular housing (FIG. 7). The additional resistance to sliding movement of the plunger 137 caused by engagement of the front rib on the plunger with the rib 145 in the bore will indicate when the vent slot 143 is about to be uncovered and withdrawal of the plunger should be stopped. The cannula 123 of the vent control device can then be removed from the stopper of the blood culture bottle, and, through movement of the plunger, the liquid can be accurately discharged through the cannula 123 onto a specific location on a culture plate.

When the vent control device 111 is used to relieve pressure build-up in a blood culture bottle during anaerobic culturing, the plunger 137 is positioned near the needle hub end of the central bore 118 as shown in FIG. 9, so that it blocks the bypass slot 143 and prevents air from bypassing the plunger. The growth of bacteria in the blood culture bottle during incubation creates gases such as carbon monoxide, carbon dioxide, methane, etc., causing pressures as high as 80 psi to develop in the blood culture bottle. Pressures of this magnitude may blow the stopper out of the blood culture bottle, presenting a physical hazard to personnel and creating unsanitary conditions in the laboratory.

When the cannula 123 of the vent control device 111 extends through the stopper and into a blood culture bottle undergoing anaerobic culturing, a pressure build-up in the bottle will move the plunger 137 along the central bore 118 of the housing 113 in the direction of the arrow A, FIG. 9, until the plunger uncovers the slot 143. When the slot 143 is uncovered, gases will escape through the air permeable membrane 133, thus relieving pressure in the blood culture bottle and preventing blowout of the plunger 137. The membrane 133 will further protect the bottle contents against contaminated air in the event the pressure build-up decreases and air is drawn back into the blood culture bottle. Subculturing can be accomplished in the same manner as described for aerobic blood culture bottles.

I claim:

1. A vent control device for use with a blood culture bottle containing a culture medium and having a pierceable stopper sealing the bottle through which a blood sample may be injected, the vent control device including:

a tubular housing having a central bore with an opening at each end thereof, a cannula connected to one end of the housing and projecting outwardly of the housing, for connecting the vent control device to the interior of the bottle by piercing the bottle stopper without exposing the bottle contents to atmospheric contamination, and a vent control element closing the opening at the opposite end of the housing, the vent control element including a thin sheet of an air permeable sterile filter material releasably adhered to the housing to permit removal thereof for subsequent subculturing.

2. The vent control element of claim 1 in which the thin sheet of filter material is a spun bonded olefin.

3. The vent control element of claim 1 in which the thin sheet of filter material is adhered to the tubular housing by a thermoplastic coating.

4. A vent control and subculturing device for use with a blood culture bottle containing a culture medium and having a piercable stopper sealing the bottle through which a blood sample may be injected into the bottle and blood culture medium removed from the bottle for subculturing, the device including:

a housing having a central bore with an opening at each end thereof, a cannula connected to an opening at one end of the housing and projecting outwardly of the housing for connecting the device to the interior of a blood culture bottle by piercing the bottle stopper without exposing the bottle's contents to atmospheric contamination, a plunger mounted in the central bore of the housing in sealing slidable relation thereto for selectively sealing and opening communication between the opposite ends of the housing bore upon movement of the plunger between two axially displaced positions in the housing bore, means formed in the outer end of the plunger for attachment to a plunger rod so that the plunger can be reciprocated in the central bore of the housing to withdraw blood culture medium from the culture bottle, thereby permitting accurate subculturing upon removal of the cannula from the blood culture bottle stopper, a plunger bypass interconnecting the opposite ends of the housing bore when the plunger is in its open position, and a thin sheet of air permeable sterile filter material releasably adhered to the end of the housing opposite the cannula and covering the opening at that end of the housing.

5. The vent control and subculturing device of claim 4 in which the plunger bypass permits communication between the opposite ends of the housing bore only when the plunger is located at the end of the central bore adjacent the filter.

6. The vent control and subculturing device of claim 5 in which the bypass is a slot formed in the inner surface of the wall of the tubular housing and extends inwardly from the end of the housing adjacent the filter for a distance greater than the length of the plunger.

7. The vent control and subculturing device of claim 4 in which the plunger is movable from its sealing position to its open position in response to a buildup of excessive pressure within the housing.

* * * * *